(12) United States Patent
Langford et al.

(10) Patent No.: US 7,283,243 B2
(45) Date of Patent: Oct. 16, 2007

(54) SEMICONDUCTOR DIODE LASER SPECTROMETER ARRANGEMENT AND METHOD

(75) Inventors: Nigel Langford, Glasgow (GB); Geoffrey Duxbury, Glasgow (GB); Erwan Normand, Glasgow (GB)

(73) Assignee: Cascade Technologies Limited, Glasgow (GB)

(*) Notice: Subject to any disclaimer, the term of this patent is extended or adjusted under 35 U.S.C. 154(b) by 471 days.

(21) Appl. No.: 10/511,041

(22) PCT Filed: Apr. 8, 2003

(86) PCT No.: PCT/GB03/01510

§ 371 (c)(1),
(2), (4) Date: Oct. 12, 2004

(87) PCT Pub. No.: WO03/087787

PCT Pub. Date: Oct. 23, 2003

(65) Prior Publication Data

US 2005/0157303 A1 Jul. 21, 2005

(30) Foreign Application Priority Data

Apr. 9, 2002 (GB) .................................. 0208100.8

(51) Int. Cl.
*G01N 21/00* (2006.01)
(52) U.S. Cl. .................................. 356/439; 250/339.01
(58) Field of Classification Search ........ 356/437–439, 356/326–328; 250/336.1
See application file for complete search history.

(56) References Cited

U.S. PATENT DOCUMENTS 5,636,035 A 6/1997 Whittaker et al.

FOREIGN PATENT DOCUMENTS

| DE | 43 31 847 A1 | 4/1994 |
| EP | 0 877 454 A1 | 11/1998 |

OTHER PUBLICATIONS

Bracewell, "The Fourier Transform and its Applications," pp. 177-180, 1965.
Patent Abstracts of Japan, Jul. 27, 1988, Abstract of JP 63182550.
Namjou et al., "Sensitive Absorption Spectroscopy with a Room Temperature Distributed Feedback Quantum Cascade Laser," Optics Letters Vo. 23, No. 3, pp. 219-221, 1998.
Duxbury, "Infrared Vibration-Rotation Spectroscopy," Chapters 5 and 9, 2000.
Kosterev et al., "Trace-gas Detection in Ambient Air with a Thermoelectrically Cooled, Pulsed Quantum-Cascade Distributed Feedback Laser," Applied Optics Vo. 39, No. 36, pp. 6866-6872, Dec. 2000.
Werle et al., "Near and Mid-Infrared Laser-Optical Sensors for Gas Analysis," Optics and Lasers in Engineering, pp. 101-114, 2001.
Webster et al., "Quantum-Cascade Laser Measurements of Stratospheric Methane and Nitrous Oxide," Applied Optics, vol. 40, No. 3, pp. 321-326, Jan. 2001.

(Continued)

*Primary Examiner*—Tarifur Chowdhury
*Assistant Examiner*—Jonathan D Cook
(74) *Attorney, Agent, or Firm*—Dicke, Billig & Czaja, PLLC

(57) ABSTRACT

A method apparatus for sensing gases using a semiconductor diode laser spectrometer, the method comprising: introducing a sample gas into a non-resonant optical cell (17); applying a step function electrical pulse (19) to a semiconductor diode laser (20) to cause the laser (20) to output a continuous wavelength chirp for injecting (16a) into the optical cell (17); injecting (16a) the wavelength chirp into the optical cell (17); using the wavelength variation provided by the wavelength chirp as a wavelength scan, and detecting (23) light emitted from the cell (17), wherein a chirp rate is selected to substantially prevent light interference occurring in the optical cell (17).

27 Claims, 11 Drawing Sheets

OTHER PUBLICATIONS

Beyer et al., "Compact System for Gas-Measurements with Quantum-Cascade-Lasers," Third International Conference on Turntable Diode Laser Spectroscopy, Jul. 2001.

Normand et al., "Characterisation of the Spectral Behaviour of Pulsed Quantum Cascade Lasers using a High Resolution Fourier Transform Infrared Spectrometer," Optics Communications, 197, pp. 115-120, Sep. 15, 2001.

Kosterev et al., "Transportable Automated Ammonia Sensor Based on a Pulsed Thermoelectrically Cooled Quantum-Cascade Distributed Feedback Laser," Applied Optics, vol. 41, No. 3, Jan. 20, 2002.

International Search Report for Application no. PCT/GB03/01510.

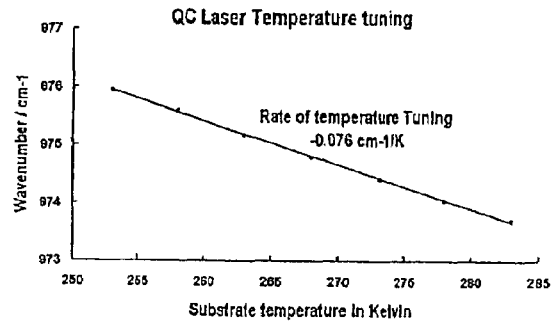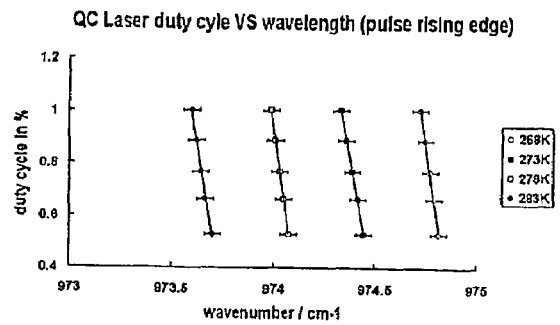
Fig.6a  Fig.6b
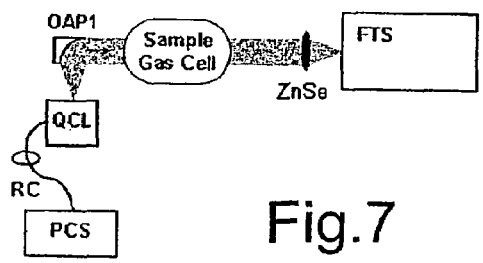
Fig.7
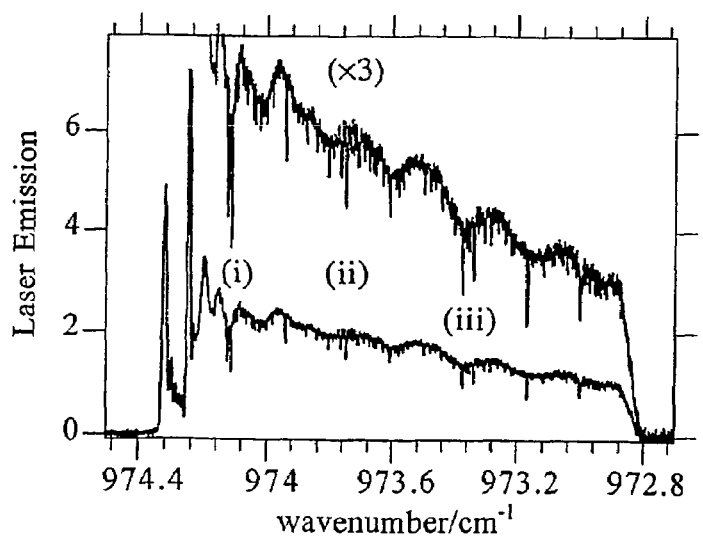
Fig.8

SEMICONDUCTOR DIODE LASER SPECTROMETER ARRANGEMENT AND METHOD

BACKGROUND

The present invention relates to a semiconductor diode laser spectrometer arrangement and in particular an infrared semiconductor diode laser spectrometer having time resolved absorption, in which the wavenumber scale calibration is based on a time to wavenumber/cm$^{-1}$ mapping.

Infrared absorption spectrometers are used for detecting and measuring gases. Infrared semiconductor diode lasers are used extensively to provide the light to be absorbed by the measurement species, as these lasers are relatively small, spectrally well defined, bright and tunable. Further advantages of these lasers over other lasers exist, some of which can be seen in spectroscopic monographs.

In remote locations and harsh environments, one of the most effective and accurate methods of trace gas sensing uses semiconductor diode laser based spectrometers. Although gas sensing has been undertaken for some decades, in many environments it remains difficult to remotely monitor trace gas constituents.

Many previous instruments have slow response times, are frequently bulky, unreliable, expensive, and require constant maintenance.

In order to retrieve information with known technology, remote sensing of gases usually takes place in the near and mid-infrared region of the electromagnetic spectrum, where the chemical fingerprints of most chemical compounds lie. By near and mid-infrared, it is meant radiation having a wavelength in the range of 1 μm to 14 μm. This spectral region contains highly transmitting windows, so-called "atmospheric windows", which owe their transparency to the low density of strong absorption lines of $CO_2$ and $H_2O$. These atmospheric windows are of great interest for spectroscopy since the absorption lines of strongly absorbing trace molecules have similar or greater intensity than the weak lines of $CO_2$ and $H_2O$.

Near-infrared diode lasers produce light in the wavelength range of the vibrational overtones, about 1 μm to 3.0 μm. Since the absorption coefficients of the vibrational overtones are much smaller than those of the fundamental bands, the sensitivity of spectrometers that use such lasers remains limited. Thus, the sensitivity of such gas sensing apparatus rarely achieves the sub-part per billion (sub-ppb) range.

Mid-infrared diode lasers produce light in the wavelength range of the fundamental rotation-vibration bands, about 3 μm to 14 μm. These lasers have not been as technologically developed as those in the near infrared region, and hence have low single mode output power, Gas sensing systems based on mid-infra-red diodes are capable of achieving sub-ppb sensitivity. The development of such light sources has, therefore, been wholly dedicated to spectroscopic applications. Several disadvantages are associated with conventional mid-infrared diode lasers, principally lead salt lasers, such as low output power, and their need to be cryogenically cooled to 77 K or to even lower temperature. Thus, they require a bulky and expensive operating system to maintain this temperature.

Recently, room temperature and high light output power operation has been achieved in the mid-infrared using quantum cascade (QC) lasers. Unlike preceding lasers, QC lasers are unipolar semiconductor lasers that can be designed to emit at any desired wavelength in the mid-infrared. Replacement of lead salt lasers by QC lasers provides the potential to improve both the detection sensitivity and spectral resolution of mid-infrared absorption spectrometers.

The QC laser based spectrometers developed so far use two main approaches. The first uses a continuous wave (CW) operating QC laser as a "drop-in" replacement for a lead salt laser. The second approach is to use a pulsed QC laser in a way that mimics the use of a continuously operating laser. In some experiments conducted by Webster et al (Applied Optics LP 40, 321 (2001)), the first approach was used with one of the lead salt diode lasers in an ALIAS II spectrometer being replaced by a QC laser. Test measurements made using an ER2 aircraft platform showed that the QC laser could successfully replace a lead salt laser and was less affected by temperature instability. However, for CW operation the laser needed to be operated at 77 K. The second method was described originally by Whittaker et al (Optics Letters 23, 219 (1998)). In this method a very short current pulse is applied to a QC laser operating near room temperature to provide a narrow wavelength pulse. In this mode of operation the spectral resolution is limited by the wavelength up-chirp. Thus, in this type of spectrometer the wavelength up-chirp is regarded as detrimental to the operation of the system.

The wavelength up-chirp ("effective emission linewidth") is induced by the temporal duration of the drive current/voltage pulse. By the term "effective emission linewidth", it is meant the observable/measurable spectral width (FWHM) of the emission of a semiconductor diode laser induced by an applied current/voltage pulse to its electrical contacts.

For example, if the duration of the pulse applied to a QC laser were of the order of 10 ns, the effective emission linewidth would be of the order of 700 MHz (0.024 cm$^{-1}$) in the spectral domain (Optics Letters 23, 219 (1998)).

In order to scan samples using a pulsed QC laser based spectrometer, the effective emission linewidth is runed across a spectral region using a slow DC current ramp superimposed on the pulse train. This means that the resultant spectral tuning is a quadratic function of the DC current ramp injected to the laser [Optics Letter 23, 219 (1998); Applied Optics 39 6866 (2000); Applied Optics 41, 573 (2002)]. A problem with this approach is, however, that an additional step is needed in the data processing stage, to correct for the quadratic effect. In some cases, to improve the signal to noise ratio, (Optics Letters 23, 219 (1998)), a small AC current modulation signal is added to the DC ramp in order to use phase sensitive detection of the detected optical signal.

Whilst adding this modulation may increase sensitivity, it requires the use of demodulation in the detection system, so rendering the system more complex. A further problem with this is that the use of a modulation inherently reduces the scan rate, since the high speed detected signals are demodulated to low audio frequencies signals. Hence, prior art arrangements of this type allow scan rates only of the order of tens of Hertz. One system proposed by Beyer et al (Third International Conference on Tunable Diode Laser Spectroscopy Jul. 8-12 2001, Zermatt Switzerland) uses the wavelength variation of the intrinsic wavelength chirp. However, the arrangement proposed is of limited use for chemical finger printing.

In both the CW operated laser (first method) described by Webster et al (Applied Optics LP 40, 321 (2001)) and the short pulse (second method), described originally by Whittaker et al (Optics Letters 23, 219 (1998)), for a gas with a small absorption coefficient the simplest way of achieving an observable change in the transmitted signal is to use a long sample length. This can be achieved by use of either resonant or non-resonant optical cells. Resonant cell schemes are complicated and require sophisticated techniques to minimise the effects of back-reflected signals from the input mirror to the cell disrupting the performance of the laser. Non-resonant cells, such as the so-called Herriot cell or astigmatic Herriot cell are attractive as they offer long path lengths, without the penalty of back-reflected signals. In addition, the path length is independent of the concentration of the gas in the cell. A major drawback associated with non-resonant cells is the occurrence of "fringing" due to the partial overlap of the beams that propagate around the cell. This decreases significantly the system performance.

As can be seen, known spectrometers using semiconductor diode lasers, in particular quantum cascade (QC) lasers, have shortcomings, which limit their use for absorption spectroscopy in pulsed operation. Specifically prior art QC laser based spectrometers, where the light sources have to be driven in pulsed mode operation to achieve room temperature operation, have the resolution of their effective emission linewidth determined by the temporal duration of the drive voltage/current pulse applied to its electrical contacts.

An object of the present invention is to overcome at least one of the aforementioned problems.

SUMMARY

Various aspects of the invention are defined in the independent claims. Some preferred features are defined in the dependent claims.

According to one aspect of the invention there is provided a fringe free method for sensing gases using semiconductor diode laser spectrometer. This involves introducing a sample gas into a non-resonant optical cell and injecting light from a semiconductor laser into the cell. This light is generated by applying a one or a series of substantially step function electrical pulses to a semiconductor diode laser to cause the laser to output one or more pulses, each having a continuous wavelength chirp, for injecting into the optical cell.

Preferably, each applied pulse has a duration that is greater than 150 ns, in particular greater than 200 ns.

Preferably, each applied pulse has a duration that is in the range of 150 to 300 ns, preferably 200 to 300 ns. This can provide a tuning range of about 60 GHz. The chirp rate is selected so that there is a time delay between spots on the reflecting elements of the non-resonant cell sufficient to substantially prevent light interference from occurring, wherein the spots define locations at which the injected chirp is reflected from the cell walls. The wavelength variation provided by the wavelength chirp itself is used to provide a wavelength scan. Hence, there is no need to tune the effective emission linewidth across a spectral region using, for example, a slow DC current ramp superimposed on the pulse train. Light output from the optical cell is detected using a suitable detector.

Preferably, each detected pulse has a duration that is greater than 150 ns, in particular greater than 200 ns.

Preferably, each detected pulse has a duration that is in the range of 150 to 300 ns, preferably 200 to 300 ns.

Alternatively, rather than using a non-resonant cavity, the gas sample may be unconfined, and the method for sensing may use an open path configuration to prevent light interference from occurring. In either case, by preventing light interference from occurring, fringing effects can be avoided. This means that the sensitivity of the method can be significantly improved.

BRIEF DESCRIPTION OF THE DRAWINGS

Various aspects of the invention will now be described by way of example only and with reference to the accompanying drawings, of which:

FIG. 6a shows a plot of wavenumber versus temperature;

FIG. 6b shows a plot of wavenumber versus duty cycle;

FIG. 7 is a block diagram of a system for sensing gases that includes a QC laser and a Fourier transform Spectrometer;

FIG. 8 shows an absorption spectrum of 1,1 difluoroethylene, $CF_2CH_2$, recorded using the apparatus of FIG. 7;

DETAILED DESCRIPTION

The spectrometer in which the invention is embodied advantageously uses the wavelength up-chirp exhibited by pulsed QC and semiconductor lasers to provide a wavelength scan. Each individual pulse output by the laser provides a wavelength variation, i.e. a wavelength scan, by virtue of the wavelength up-chirp. This wavelength up-chirp is induced by a heating effect occurring for the entire duration of the applied current/voltage drive pulse. For these QC lasers, the wavelength up-chirp has been shown to be continuous.

More specifically, under particular conditions of the electrical drive pulse shape (Optics Communications 197, 115 (2001)), the spectral behaviour of pulsed QC lasers is characterised by the fact that this wavelength up-chirp is almost linear with respect to time. It has further been shown that in pulsed operations the spectral behaviour of QC lasers can be mapped to the temporal definition of the applied drive current/voltage pulse to its electrical contacts. In view of this, it is possible to map the light output temporal behaviour of a QC laser and to show it in the time domain with a photodetector.

FIGS. 1a to 1g show computer simulated plots of the temporal and spectral responses for single mode and multimode semiconductor diode lasers when a square current/voltage signal is applied to their electrical contacts. For the purposes of this description, the term temporal response means the time taken for the detection system to achieve a deflection on a range proportional to an electrical signal, in the shape of a perfect step function, applied to its input. The temporal response is calculated using the usual equation for the relation between the rise time and the bandwidth of a system, i.e. temporal response=rise time=0.35/bandwidth.

Figure 1A:
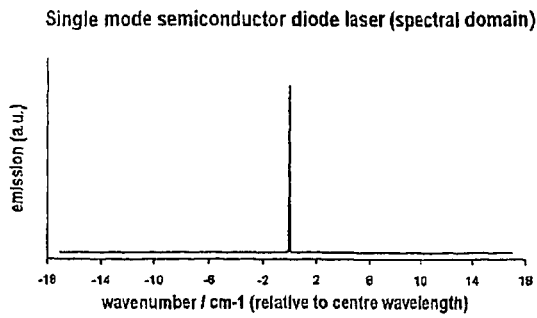
FIGS. 1a to 1f show computer simulated plots of emission versus wavenumber for various modes of operation of a QC laser.
Figure 1B:
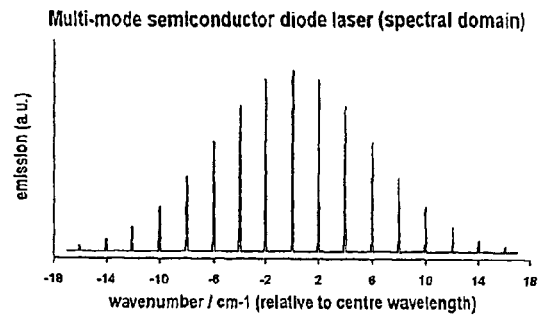

FIGS. 1a and 1b show computer simulated results for the spectral behaviour at a fixed moment in time so that no chirp is observed in the spectral domain and that the represented emission linewidth is the intrinsic emission linewidth. By the term "intrinsic emission linewidth", it is meant the instantaneous observable/measurable spectral width (FWHM) of the emission. The intrinsic emission linewidth of a semiconductor diode laser is usually much smaller than the effective emission linewidth and can be difficult to quantify under pulsed operation.

Figure 1C:
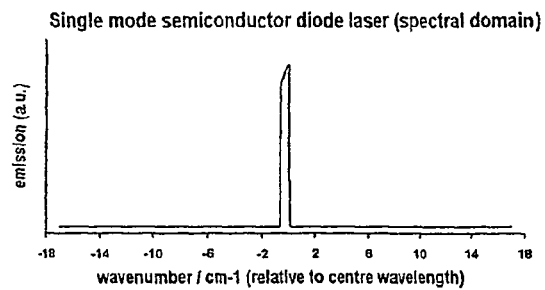
Figure 1D:
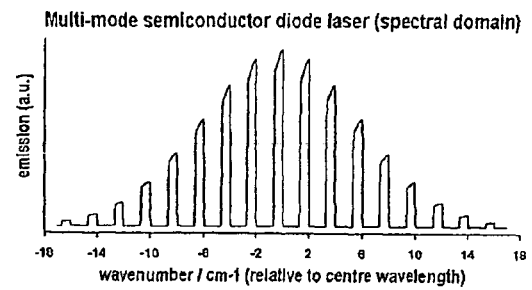
Figure 1E:
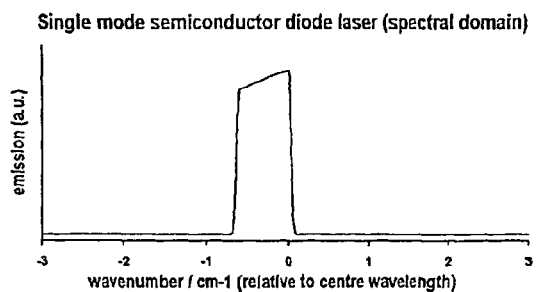
Figure 1F:
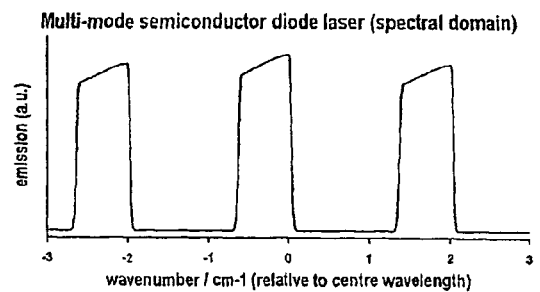
Figure 1G:
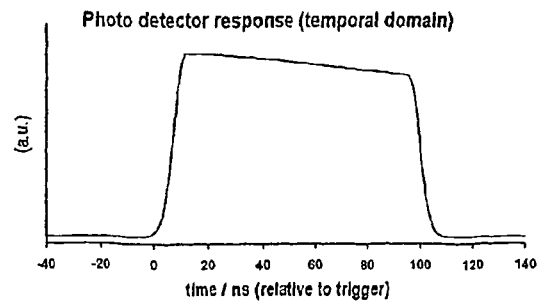
FIG. 1g shows a computer simulated plot of emission versus time for a QC laser in a particular mode of operation.
Figure 1H:
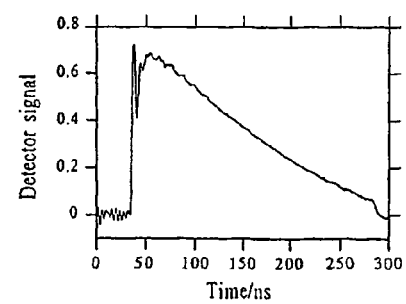
FIG. 1h shows an experimental plot of emission versus time for a QC laser that is being operated so as to generate a chirp.

FIGS. 1c and 1d show computer simulated results achieved on the application of a well-defined rectangular current/voltage drive pulse with a duration sufficiently long so that a chirp is observed towards longer wavelength. As mentioned previously, this chirp arises from heating effects induced by the drive pulse. The amplitude decay that goes with this chirp is caused by the reduced efficiency of lasing action as the heating increases. The effect of the wavelength chirp can be seen more clearly in FIGS. 1e and 1f. A computer simulation of the temporal behaviour of the emission is shown in FIG. 1g. Since the amplitude decay of the chirp decreases with time, the temporal response is a mirror image of that in the spectral domain. FIG. 1b shows experimental results for a laser that is pulsed in such a manner that a chirp is generated. From a comparison of FIGS. 1g and 1h, it can be seen that there is a correlation between the theoretical and the simulated plots.

Figure 2:
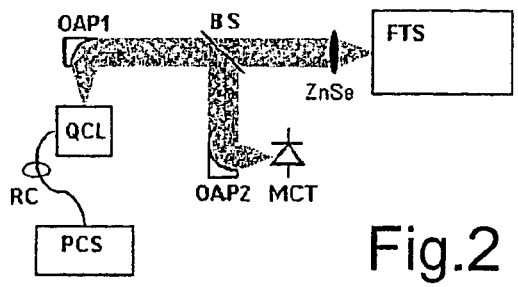
FIG. 2 is a schematic diagram of an arrangement for characterising a semiconductor laser using a scanning Fourier transform spectrometer.

FIG. 2 shows an arrangement for characterising the spectral output behaviour of semiconductor diode lasers using a continuous scanning infrared Fourier transform spectrometer. The results of experiments using this arrangement are shown in FIGS. 3-6.

Figure 3A:
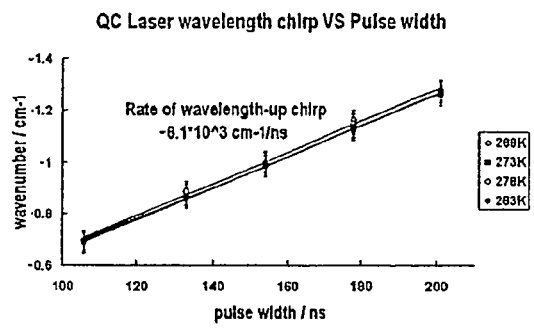
FIG. 3a shows plots of wavenumber versus pulse duration at various different temperatures.
Figure 3B:
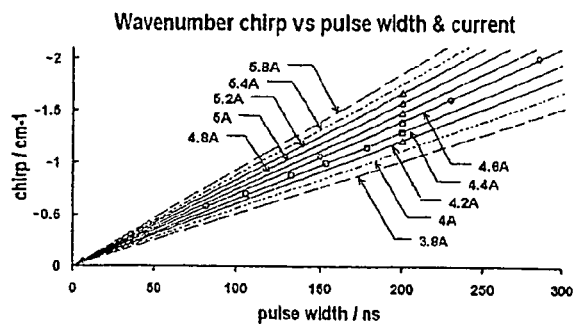
FIG. 3b shows plots of wavenumber versus pulse duration at various different current amplitudes.

FIG. 3a is a plot of wavenumber chirp as a function of the temporal duration of the applied current pulse (fixed amplitude 4.2 A) for a range of substrate temperatures. The results indicate that the rate of tuning, over the temperature range investigated, is insensitive to temperature. From this plot the rate of change of wavenumber as a function of time, $\beta$, can be determined empirically. To vary $\beta$, the amplitude of the current/voltage pulse must be altered, as illustrated in FIG. 3b. From this, it can be seen that irrespective of the applied current, over the range of currents used, $\beta$ is almost linear in nature.

Figure 4A:
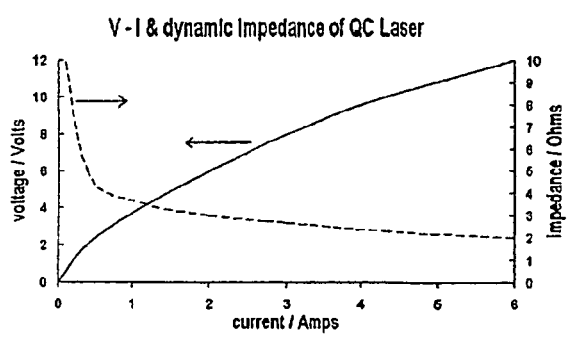
FIG. 4a shows a plot of dynamic impedance of a QC laser.
Figure 4B:
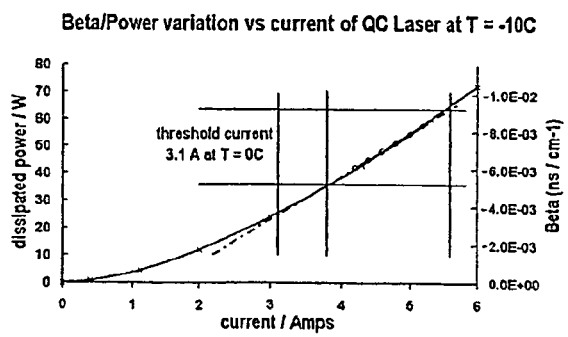
FIGS. 4b and 4c show plots of dissipated power versus current for a QC laser at –10 C.
Figure 4C:
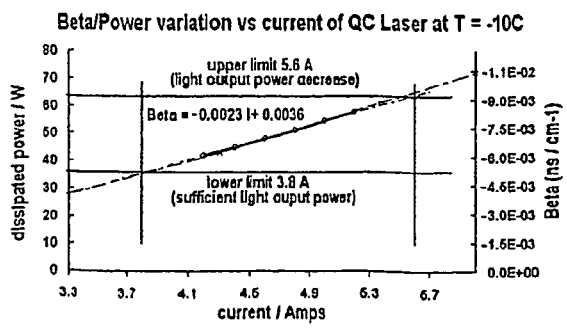
Figure 5:
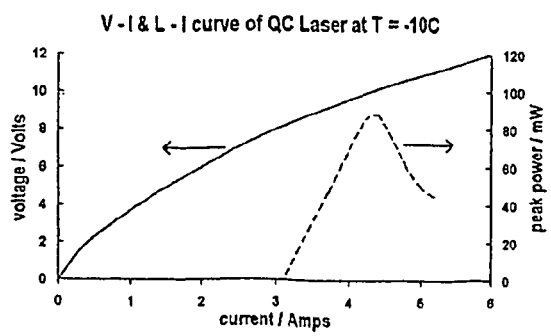
FIG. 5 is a plot of voltage and power as a function of current for a QC laser operating at a temperature of –10 C.

$\beta$ is related to the power dissipated inside the laser diode and the almost linear variation in $\beta$ arises from the fact that the QC laser exhibits a dynamic impedance, as shown in FIG. 4a, which results in a almost linear power dissipation over the current range used, see FIG. 4b. It should be noted that the value of $\beta$ is determined over the temporal range for which the output shows no transient behaviour, see FIG. 4c. The limiting values of $\beta$ are defined, at the lower end, by the current/voltage amplitude necessary to achieve a usable output power and at the upper end, by the current/voltage amplitude that induces a reduction in the output power, see FIG. 5. The starting wavenumber of the wavenumber chirp is influenced by both the substrate temperature of the QC laser and the duty cycle of the applied current/voltage pulses as shown in FIGS. 6a and 6b. Hence, by varying the substrate temperature and/or the duty cycle, the starting wavenumber can be altered.

As will be appreciated, the effectiveness of a gas spectrometer that uses a wavelength-chirp to provide a wavelength variation for scanning a sample depends on the actual range of wavelengths over which the chirp extends. This wavelength range may correspond to a frequency variation of 60 GHz. FIG. 7 shows an arrangement for measuring the upper limits of the effective line width of a QC laser. This is based on a Fourier transform spectrometer, which is adapted to generate spectra representative of the output from a sample cell into which light from a QC laser is injected. Fourier transform based spectrometers are well known and use Michelson interferometers. To measure accurately the current supplied to the QC laser, a Rogowski coil is provided. A typical spectrum measure using the arrangement of FIG. 7 is illustrated in FIG. 8, which shows a high resolution absorption spectrum of 1,1 difluoroethylene, $CH_2CF_2$. In this case, the resolution of the spectrometer is 0.0015 cm⁻. The duration of the electrical drive pulse applied to the QC laser was 200 ns, the pulse repetition frequency, 20 kHz, and the drive current 4.8 A. The substrate temperature was −1.5° C. From FIG. 8, it can be inferred that the upper limit of the laser linewidth is that set by the instrument resolution, i.e. in this case 45 MHz. Also, it can be seen that over the wavelength scan range of the QC laser chirp three groups, i.e. (i), (ii) and (iii), of lines of $CH_2CF_2$ can be easily identified. This demonstrates that the effective resolution of a pulsed QC laser spectrometer is sufficient to detect chemical fingerprints for at least some chemicals.

Figure 9:
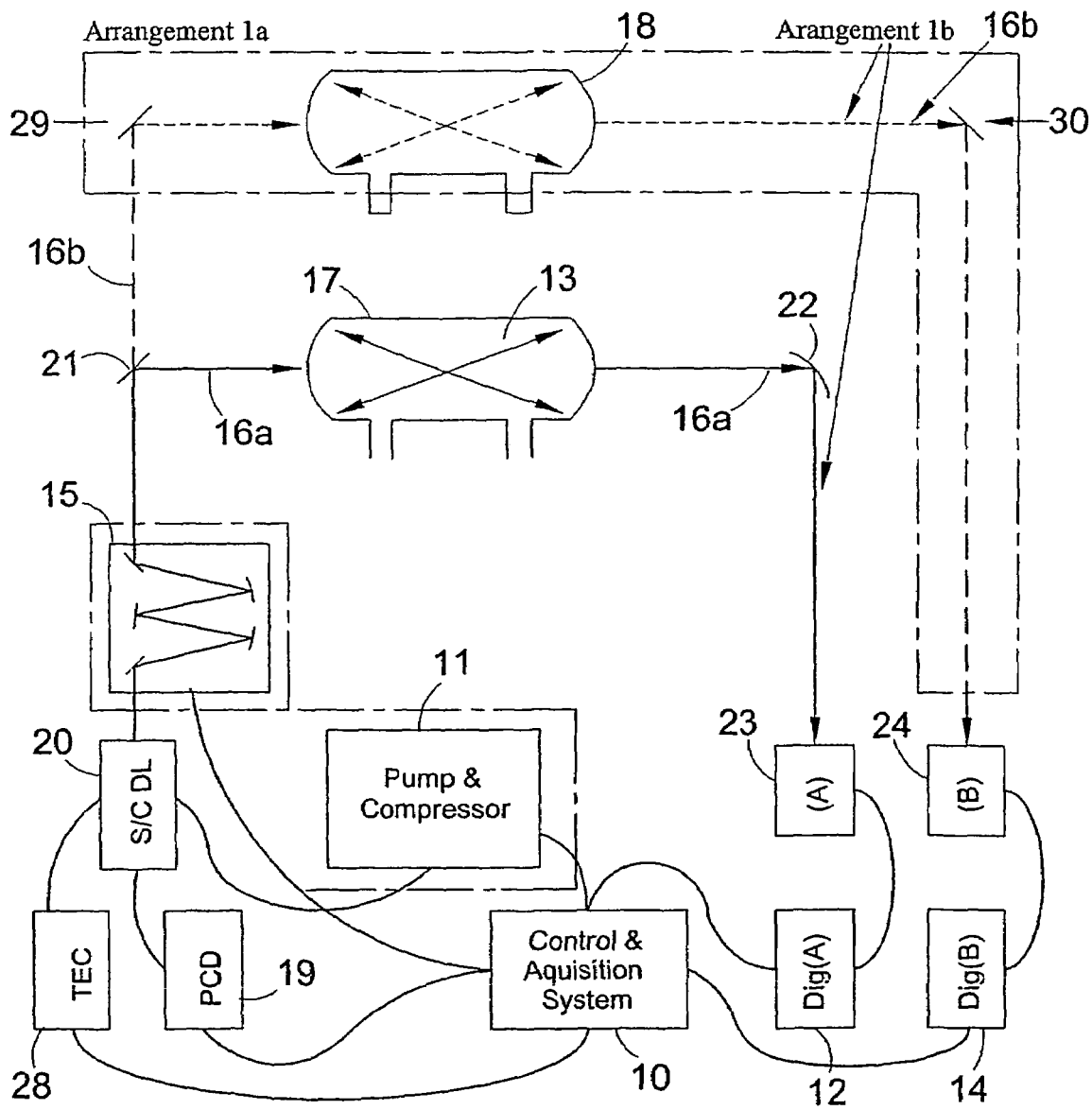
FIG. 9 is a block diagram of another spectrometer.

Because of its controllable and predictable characteristics, the almost linear wavenumber down-chirp can be exploited to make spectral measurements. In particular, the almost linearity of the wavenumber chirp as a function of time allows the construction of a high speed, sub-microsecond, semiconductor diode laser absorption spectrometer. FIG. 9 shows two spectrometer arrangements 1a and 1b for measuring radiation absorbed by a species, i.e a gas sample. In the low intensity limit, the spectrometer determines the absorption coefficient of a species by measuring the ratio of the intensity of the light incident on the sample gas cell, $I_o$, and that transmitted through a sample gas cell containing the absorbing species, $I_a$. In the low intensity limit, the change in the intensity of light that passes through the gas is described by the Beer-Lambert relationship, $I_a=I_o\exp(-\alpha L)$, with $\alpha$ the absorption coefficient and L the optical path length. It should be noted that $\alpha$ is a function of wavenumber and is independent of the intensity at low intensities of the incident radiation.

The spectrometer of FIG. 9 uses a closed non-resonant optical cell (confined gas) configuration and comprises a current/voltage drive pulse generator 19 that is connected to an input of a laser 20. The pulse generator 19 is operable to apply substantially rectangular pulses to the laser 20. In this case, the laser 20 is a single mode semiconductor diode quantum cascade laser (QC laser). The laser 20 is housed in a Peltier temperature controlled enclosure (not shown). The Peltier element is controlled by a thermoelectric controller 28. Connected to the laser enclosure is a compressor and pump unit 11, which is used to cool/heat fluid and circulate that fluid into the hollow housing of the diode laser enclosure 20. This enables the laser element to be operated over a wider temperature range than is possible using solely the Peltier element.

On an optical path from the laser 20 output is an optional spectral filter 15, for example a small grating monochromator, which may be used to provide a single mode laser output if a multi-longitudinal mode laser is used. On an optical path from the filter are two beam splitters 21 and 29 respectively. These could be, for example, germanium beam splitters for laser radiation at wavelengths close to 10 μm. However, it will be appreciated that any other suitable splitters could be used. The first beam splitter 21 is positioned so as to direct at least some of the light incident thereon into a first optical sample cell 17, which contains the sample that is to be sensed or characterised, and transmit the rest of the light to the second beam splitter 29. The second beam splitter is positioned so as to direct at least some of the light incident thereon into a second optical cell 18, which is a reference cell. The cells 17 and 18 have the same characteristics. Both are non-resonant optical cells. The cells 17 and 18 may be Herriot cells, either standard or astigmatic Herriot cells.

In the arrangement of FIG. 9, radiation emitted by the QC laser can traverse two possible optical paths, 16a and 16b, one through the sample cell 17 and one through the reference cell 18. In order to detect radiation transmitted through each of these cells, detectors 23 and 24 are provided at the respective outputs. Connected to each of these is a digitiser 12 and 14 respectively, each of which in turn is connected to a control and acquisition system 10, which provides overall control of the spectrometer. In addition to the digitisers, the control system 10 is connected to each of the current/voltage drive pulse generator 19, the spectral filter 15, and the pump and compressor 11. As part of its functionality, the control system 10 is operable to set the amplitude and duration of the pulse applied to the laser input and monitor the resultant outputs detected from the gas and reference cells 17 and 18 respectively. The control system 10 is also operable to determine the ratio $I_a/I_o$. This could be done using, for example, Beer-Lambert's Law, which may be written as $I_a/I_o=\exp(-\alpha L)$. Of course, as will be appreciated by the skilled person, other techniques could be used.

The arrangement of FIG. 9 can be adapted for use is two separate modes: a single beam mode (SBM) or a double beam mode (DBM). In the single beam mode only the sample cell 17 is used, so that light only follows path 16a.

In this case the beam splitter 21 could be replaced by a mirror. For the SBM both $I_o$ and $I_a$ are measured using the single optical absorption cell 17. To determine Io, the cell 17 is evacuated and a series of chirped pulses from the QC laser 20 are passed through it. The output from the evacuated cell 17 is digitised by the digitiser 12, and stored by the control and acquisition system 10. To determine $I_a$, the cell 17 is filled with a sample of the gas under study 13, and the sampling process is repeated. For the dual beam method (DBM), measurement of $I_o$ and $I_a$ can be done simultaneously using both of paths 16a and 16b. In this case, the sample gas would be put in the sample cell 17 and the reference cell would be evacuated and sealed. The beams output from the gas and reference cells 17 and IS respectively are directed to the detectors 23 and 24. Detector 23 detects the absorbed light pulse output from the gas cell 17 and detector 24 detects the background light pulse output from the reference cell 18. An advantage of the DBM scheme is that by taking simultaneous measurements, the effects of drift can be minimised.

For SBM, the background light pulse with amplitude $I_o$ and the absorbed light pulse with amplitude $I_a$, each has the same distance to travel to the detection system. Providing that the optical paths lengths associated with paths 16a and 16b are identical, this is also the case for DBM, and so both pulses arrive at the detectors 23 and 24 at the same time. In either case, the absorption can be directly sensed via the use of the ratio $I_a/I_o$.

For both modes of the spectrometer of FIG. 9, that is SBM and DBM, the current/voltage drive pulse generator 19 generates a plurality of substantially rectangular pulses that are applied to the input of the laser 20. More specifically, the generator 19 provides a train of fixed amplitude sub-microsecond duration rectangular current drive pulses. This causes a fast laser heating effect and hence a continuous wavelength up-chirp of the emitted semiconductor diode laser radiation at a rate in time β. As discussed previously, the fast laser heating caused by the sub-microsecond rectangular current pulses is such that for each pulse emitted from the laser 20, the chirp is a continuous almost linear spectral variation from short to long wavelength. This is defined as a continuous spectral or wavelength scan.

As noted above, the spectrometer of FIG. 9 uses a non-resonant optical cell. As mentioned previously, the use of non-resonant cells in conventional spectrometers results in "fringing", which decreases significantly the system performance. In order to prevent this, the chirped laser spectrometer of FIG. 9 is adapted to control the light source with a chirp rate in such manner that the laser wavelength of overlapping spots in the non-resonant cell is sufficiently different to prevent interference from occurring. For some QC lasers, this can be done by dynamically varying the chirp rate. Otherwise, a laser having a suitable chirp rate has to be selected. In practice, this can be determined empirically by trial and error. By spots, it is meant regions of the reflecting elements of the cell, typically curved mirrors, of the optical cell from which light in the cavity is reflected as it bounces back and forward within the cavity. These spots are distributed over the end walls of the cells. The variation in the location of the spots arises because light is injected into the cell at different angles, and the mirrors of the cells can themselves cause a transformation of the reflection angles. By ensuring that the laser wavelength of overlapping spots is sufficiently different, the effects of residual fringing can be suppressed. The spectrometer of FIG. 9 is therefore a fringe free gas sensing system, with enhanced absorption sensitivities. As a specific example, assuming that neighbouring spots overlap and that the mirrors are spaced by 0.5 m, and that the line width of the laser is 30 MHz a chirp rate in excess of 10 MHz/ns would be sufficient to prevent interference, and thereby provide substantially fringe free performance.

Figure 10:
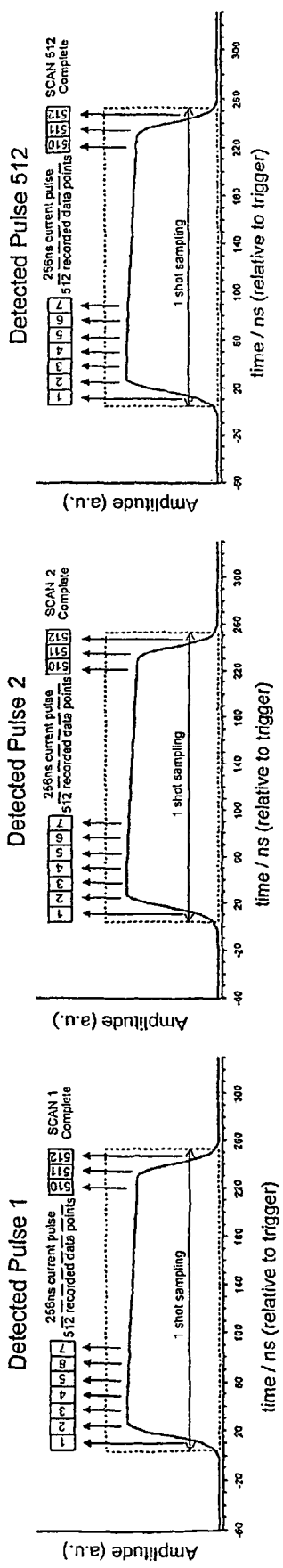
FIG. 10 shows a schematic diagram of a method of detecting optical pulses using the spectrometer of FIG. 9, and, for comparison a method used for a known spectrometer.
Figure 10:
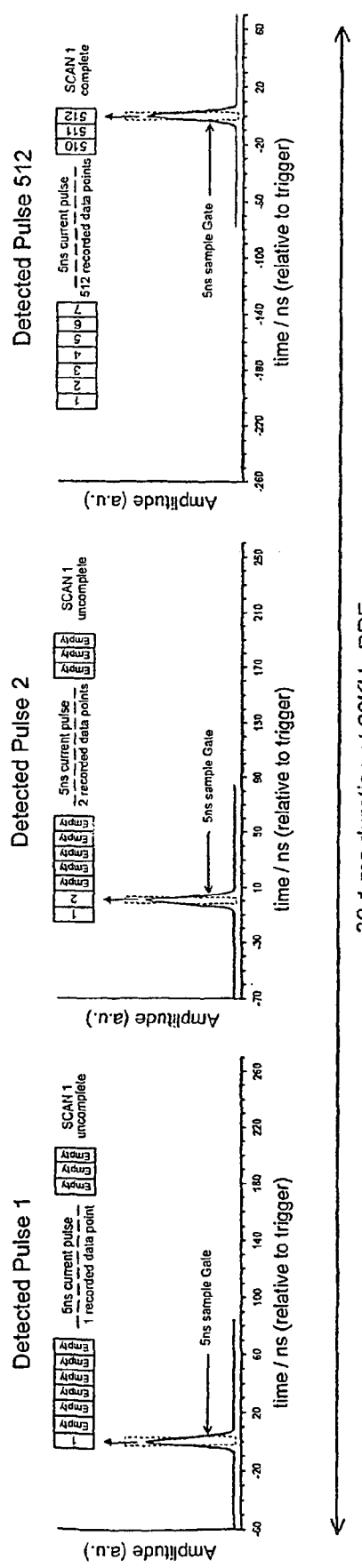
Figure 11:
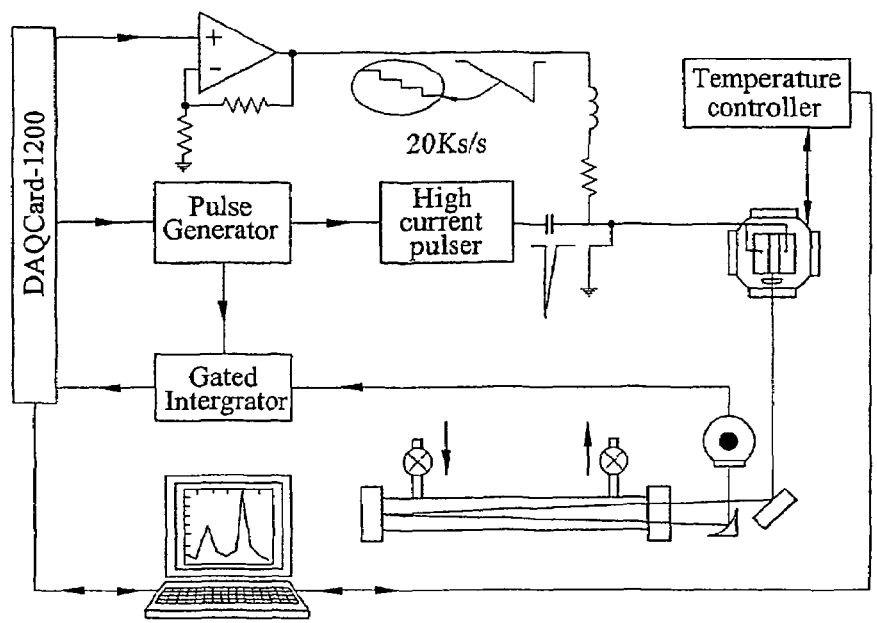
FIG. 11 is a block diagram of the prior art spectrometer used for the comparative measurements shown in FIG. 10.

FIG. 10 shows a schematic diagram of a data-sampling scheme used in the spectrometer of FIG. 9. This is referred to as Method 1. For the sake of comparison, a data-sampling scheme for a conventional QC laser spectrometer is also shown. This is referred to as Method 2. FIG. 11 shows the prior art spectrometer that, was used to implement Method 2. For the purposes of an accurate comparison the computer simulations of both systems were made using the same pulse repetition frequency (PRF) equal to 20 KHz. The PRF is the frequency at which the semiconductor diode laser has a current/voltage pulse applied to its electrical contacts. The value of 20 KHz was chosen, since it is the maximum rate at which the spectrometer of FIG. 11 can be operated (see: Applied Optics 41, 573 (2002)). It was also assumed that the spectrometer of FIG. 9 uses a 256 ns duration current/voltage pulse to exploit the wavelength up-chirp, and that the spectrometer of FIG. 11 uses a 5 ns duration current/voltage pulse (see: Applied Optics 41, 573 (2002)). For the spectrometer of FIG. 11, the effective emission linewidth is approximately 0.02 $cm^{-1}$. To provide a wavelength scan in this case, the pulse has to be continuously tuned in a non-linear manner over a 0.75 $cm^{-1}$ spectral range starting from 992.3 $cm^{-1}$. For a current amplitude similar to that used for spectrometer of FIG. 11, the spectrometer of FIG. 9 would have a parameter β of approximately $-5.9 \times 10^{-3}$ $cm^{-1}/ns$. This would give rise to a total almost linear wavelength up-chirp of 1.5 $cm^{-1}$ in 256 ns. Each chirp can therefore itself provide an entire scan.

As can be seen from FIG. 10, using the method in which the invention is embodied, that is Method 1, allows the entire spectral region to be recorded within each individual or single pulse. As shown in FIG. 10, this involves sampling the detected pulse along its entire length, thereby to obtain a range of spectral elements from that single pulse. In contrast, in Method 2 only a single spectral element may be recorded during a single pulse. Hence if the same number of sampling points, n, is recorded, e.g, n=512 which is the maximum number possible in Method 2 (see: Applied Optics 41, 573 (2002)), the theoretical improvement in signal to noise achievable in Method 1 should be $\sqrt{n}$, which for 512 point is a factor of about 22. An advantage of Method 1 is that it does not suffer from pulse to pulse fluctuations (both amplitude and temporal) inside a recorded scan since only one optical pulse is necessary. In Method 2, it has been shown that the system suffers from amplitude fluctuations of the diode laser output from pulse to pulse (see: Applied Optics 41, 573 (2002)).

Figure 12:
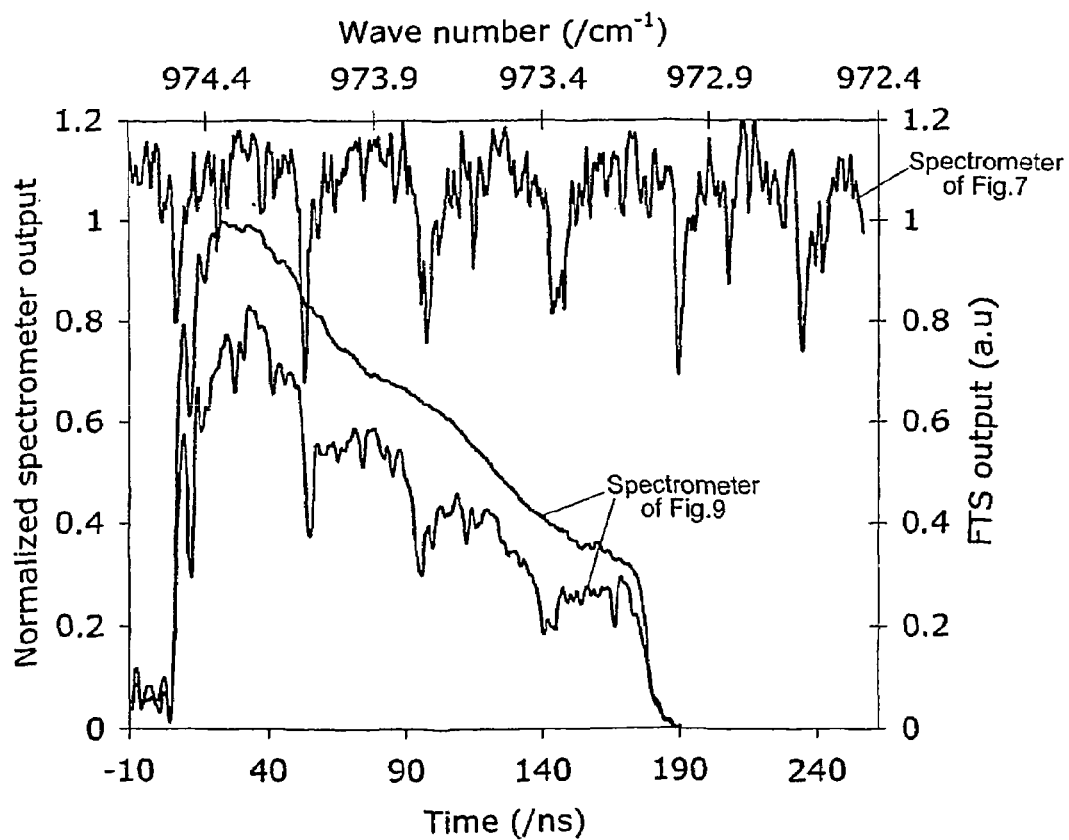
FIG. 12 shows a reference transmission spectrum of $CF_2CH_2$ and laser spectra with and without absorption by $CF_2CH_2$ obtained using the spectrometer of FIG. 9.
Figure 13:
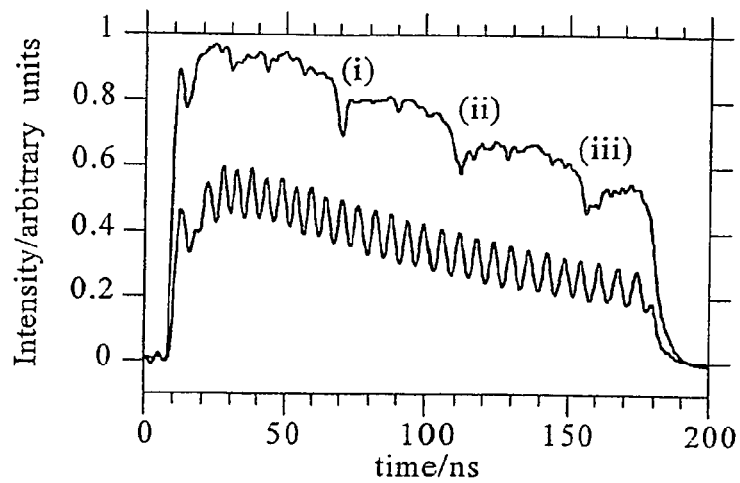
FIG. 13 shows an absorption spectrum of $CF_2CH_2$, recorded using the spectrometer of FIG. 9 (upper trace) and a recording of an etalon fringe pattern of a solid Ge etalon (lower trace)

FIGS. 12 and 13 show experimental results taken using the spectrometer of FIG. 9. In the spectrometer arrangement used for FIGS. 12 and 13, a single mode distributed feedback laser was used without a spectral filter and $I_o$ and $I_a$ were recorded using the SBM method. FIG. 12 shows measurements for a sample of 1,1 difluoroethylene ($CF_2CH_2$). The $CF_2CH_2$ spectrum in the upper trace was taken using the spectrometer of FIG. 7, but adapted to replace the QC laser with a black body source. The two lower traces taken using the spectrometer of FIG. 9 show both Io with the cell evacuated and $I_a$ with a sample of 1,1 difluoroethylene ($CF_2CH_2$) within the cell. FIG. 13 shows results for 1,1 difluoroethylene ($CF_2CH_2$) taken using the spectrometer of FIG. 9. The absorbed signal $I_a$ was recorded using an average of 4096 scans. The upper trace shows $I_a$. The lower trace is also $I_a$ but with a solid Ge etalon in place of the sample gas cell 17. This lower trace shows the etalon fringe pattern demonstrating an almost linear spectral variation from short to long wavelength. As can be seen from a comparison of the Fourier transform and diode laser spectra in FIG. 12, and the upper trace of FIG. 13 with the Fourier transform spectrum of FIG. 8, there is a strong correlation between the fingerprint patterns of difluoroethylene recorded using the two types of spectrometer. However the Fourier transform spectra in FIGS. 8 and 12, recorded using the spectrometer of FIG. 7, took more than four hours to obtain, whereas the diode laser spectra in FIGS. 12 and 13 required less than two minutes.

Figure 14:
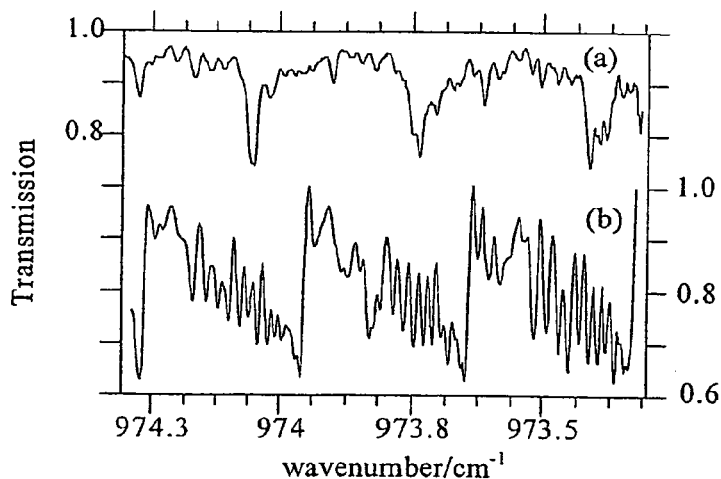
FIG. 14 shows a comparison of the absorption spectra of two different molecules (upper trace: $CF_2CH_2$; lower trace: $COF_2$) recorded using the arrangement of FIG. 9.

The wavelength range over which the chirp-induced scan occurs is sufficient to allow an identification of the chemical fingerprint of the gas to be recorded, see FIG. 14. FIG. 14 was recorded using the SBM method of the arrangement of FIG. 9. The upper trace in FIG. 14 is for 1,1, difluoroethylene ($CF_2CH_2$) and the lower trace, of the same figure, is for carbonyl fluoride ($COF_2$), FIG. 14 shows the ease of pattern recognition (identification of the chemical fingerprint) within a 200 ns time window using the spectrometer of FIG. 9. For the sake of clarity, the transmission spectra have been offset. The wavenumber calibration used a Germanium (Ge) etalon with fringe spacing 0.0483 $cm^{-1}$, and reference lines of 1,1, difluoroethylene taken from a high resolution Fourier transform spectrum using the arrangement shown in FIG. 7, except with a black body source.

In the spectrometer of FIG. 9, the bandwidth-duration product of a signal cannot be less than a certain minimum value found with the "uncertainty relation". This relationship is described in detail by Bracewell (The Fourier Transform and Its Applications, McGraw-Hill (1965)), who has proved that the product of the equivalent duration, Δt, and the equivalent bandwidth, Δν, must exceed or be equal to C, a constant that is determined by the pulse shape. For a rectangular time window $\Delta t \Delta \nu \geq C = 0.886$, and for a Gaussian time window $\Delta t \Delta \nu \geq C = 0.441$. In a short pulse spectrometer method, if the pulse duration were to be shortened there would be a Fourier transform limitation to the resolution, whereas if it were to be lengthened the wavelength chirp would be excessive. A similar analysis may be carried out for the limitations of the time resolved detection system in which the invention is embodied, as outlined below. In a time window τ the laser frequency (Λν=c; Λ is the wavelength, ν is the frequency; c is the wave velocity) will chirp by the amount ∂ν/∂t×τ, so that if a smaller time window were to be used the Fourier-limited frequency interval Δν would increase, whereas the chirp limited frequency interval would decrease. The best aperture time, τ, will therefore be determined by C/τ=∂ν/∂t×σ. Rewriting this equation in terms of Δν gives, Δν=∂ν/∂t×C/×ν, from which $\Delta \nu = \sqrt{(C \times \partial \nu / \partial t)}$. In the limiting case of C=1, and a chirp rate of $-0.0066$ $cm^{-1}/ns$, or 0.015 $cm^{-1}$. This would fall to 0.014 $cm^{-1}$ if the rectangular window function were used, and to 0.01 $cm^{-1}$ if a Gaussian time window were appropriate.

Figure 15:
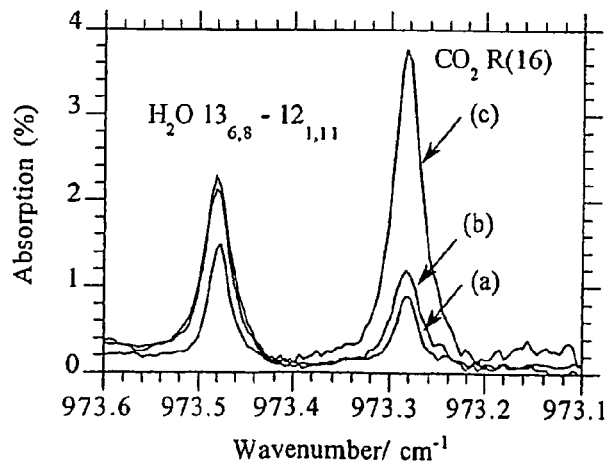
FIG. 15 shows absorption spectra for a sample of atmospheric gases, recorded using the arrangement of FIG. 9.

FIG. 15 shows the absorption spectra recorded using the SBM method of FIG. 9 for a sample of atmospheric gas. An average of 64 thousand scans was used. Trace (a) shows the results for a cell pressure 50.5 Torr. Trace (b) shows the results for a pressure of 04.5 Torr. Trace (c) shows the results for a sample to which carbon dioxide ($CO_2$) was added. In this case, the pressure was 103.2 Torr. The very low absorption coefficient line, which corresponds to $H_2O$, i.e. the peak on the left hand side of FIG. 15, has almost the same percentage absorption in traces (b) and (c). However, it is evident that a large increase in the percentage of absorption due to carbon dioxide has occurred in trace (c) in comparison to trace (b). FIGS. 14 and 15 show that it is possible to do achieve simultaneous gas measurement of different species and that it is possible to identify them (compound identification).

Figure 16:
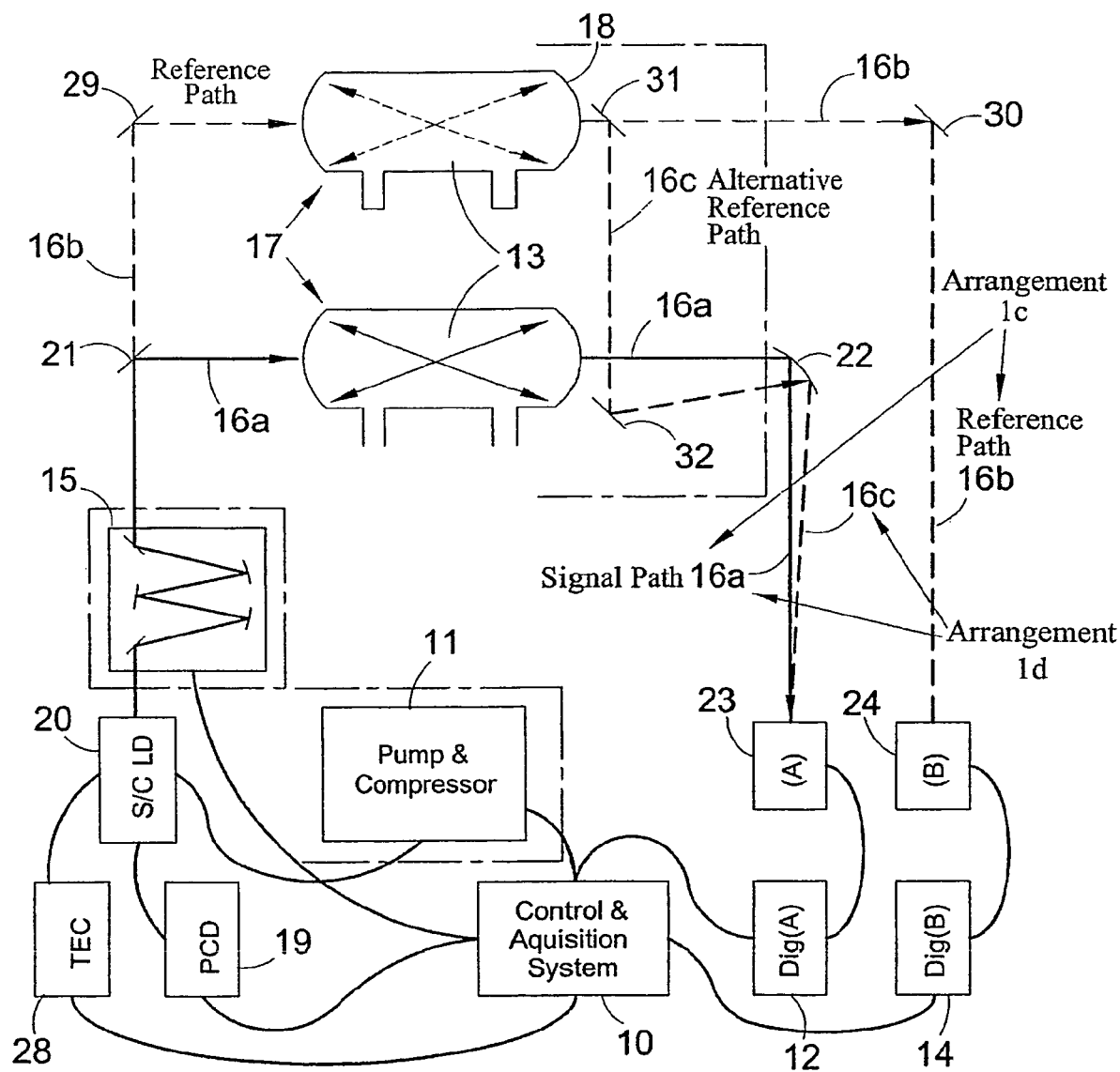
FIG. 16 is a block diagram of a modified version of the spectrometer of FIG. 9.

Various modifications to the spectrometer of FIG. 9 can be made. For example, for the double beam method, rather than having a separate reference cell that is evacuated, a reference signal could be passed through the sample cell 17 itself. This is shown in FIG. 16 as arrangement 1c. Here, the measurement path is 16a and the reference path is 16b. For the purposes of clarity, the paths 16a and 16b are shown separately in FIG. 16, but it will be appreciated that they both go through the sample cell 17. If the optical path length of the signal path, 16a, is $L_a$, and that of the reference path 16b is $L_b$, then in order to minimize absorption in the reference path 16b, La must be much greater than $L_b$ ($L_a<<L_b$). This can be arranged by, for example ensuring that the measurement beam makes many passes across the sample cell 17, whereas the reference beam either passes straight through the cell, and so makes a single pass, or only makes a limited number of passes.

The modified Beer-Lambert expression required for arrangement 1c may be derived as follows: for the signal path $I_a=I_o\exp(-\alpha L_a)$ and for the reference path $I_b=I_o\exp(-\alpha L_b)$. Hence, $\ln(I_a/I_b)=-\alpha(L_2-L_b)$. In arrangement 1c, the transit time difference between both pulses is chosen to be less than the wavelength up-chirp time or current/voltage drive pulse duration. Therefore, the background light pulse arrives at detector 24 in advance of the arrival of the signal pulse at detector 23. The outputs from the digitisers 12 and 14 are recorded, to enable the control acquisition circuit 10 to ratio them to provide $I_a/I_b$ as detailed previously. An advantage of the spectrometer of arrangement 1c of FIG. 16 is that fewer optical elements are used than in the first embodiment, arrangement 1b of FIG. 9, e.g. no reference cell. This reduces the overall size and weight of the spectrometer arrangement.

Arrangement 1d of FIG. 16 is a modification of arrangement 1c. In this case, only a single detector is used. To this end, instead of being directed into detector 24, the reference beam is directed into detector 23. The absorption path difference is identical to that of arrangement 1c, namely $\Delta L=(L_a-L_b)$. When a pulse train is incident on the beamsplitter of FIG. 16, the action of the beamsplitter is to split each individual pulse in the pulse train into two components. Any one pulse from the pulse train that follows optical path 16a has a companion pulse that follows optical path 16c. This has important consequences when considering the detection of $I_b$ and $I_a$ by the single detector arrangement 1d. To compute the ratio of $I_b$ to $I_a$ the signals corresponding to $I_b$ and $I_a$ must be recorded separately and then processed in the manner described for the SB mode of operation in FIG. 9, embodiment 1b. This means that a pulse corresponding to $I_a$ cannot arrive at the detector until its companion pulse corresponding to $I_b$ has been digitised by digitiser 12 and stored by the control and acquisition system 10. The next pulse associated with $I_b$, however, cannot arrive at the detector, before the previous $I_a$ pulse has been digitised by digitiser 12 and stored by the control and acquisition system 10. Thus, the difference in optical path length and hence transit time, between optical path 16a and optical path 16c must be greater than the distance defined by pulse temporal duration (speed of light×$t_p$) but less then the distance defined by the pulse repetition time (speed of light×$t_{rep}$)

Figure 17:
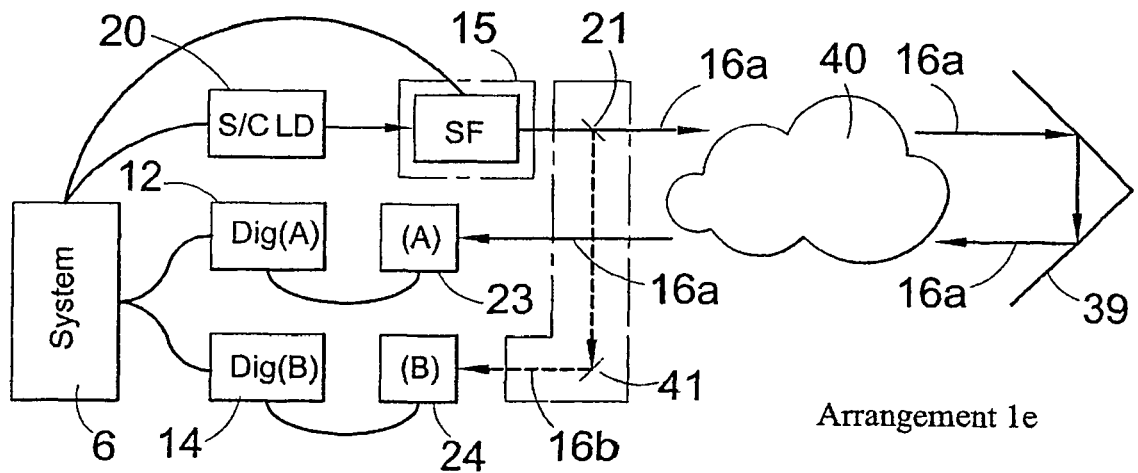
FIG. 17 is a block diagram of another spectrometer in which the invention is embodied.

All of the spectrometers described so far are closed systems, in which a sample gas is placed in a closed optical cell. However, many measurements of atmospheric trace gases have to be made using open path (unconfined gas) arrangements, i.e. the spectrometer contains no gas cell. FIG. 17 a schematic diagram of an unconfined spectrometer arrangement in which the invention is embodied. Because no optical elements are used to contain the sample gas this arrangement is fringe free. Such a spectrometer could be used, for example, as shown in arrangement 1e of FIG. 17, for monitoring the exhaust plume 40 of an engine. The arrangement of the optical components up to and including the beamsplitter 21 is identical to that of the previous embodiments 1a, 1b (FIG. 9), and 1c and 1d (FIG. 16). Opposite the filter 15 and on the optical path of beam 16a is a cube-corner retro-reflector 39 that is positioned in use so that the gas to be investigated is between the filter 15 and the reflector 39. Light reflected from the reflector 39 is directed back, through the gas towards the detection system. In contrast, the reference beam 16b is transmitted in a direction perpendicular to beam 16a through a much shorter optical path towards another reflector, which reflects it toward the detection system. In this case, the detection system is the same as for the DBM arrangement of embodiments 1b (FIG. 9) and 1c FIG. 16).

In the use of the spectrometer of FIG. 17, a stream of current pulses is applied to the laser 20, which emits light that is subsequently passed through the filter 15, thereby to produce a suitable output, i.e. that comprises a series pulses, each of which has a wavelength up-chirp. The light pulse to be absorbed 16a then travels through the exhaust plume 40 and is reflected by the retro-reflector 39, returning through the exhaust plume 40 to the spectrometer 1e. In this way, the beam 16a makes two passes through the gas. The reflected pulse 16a is then focussed onto detector 23. The background pulse of light 16b, which is focussed onto detector 24, travels via a much shorter optical path than that of the signal pulse, 16a. Hence, the transit time of the reference pulse 16b is less than that of the signal pulse 16a, so that the background pulse 16b arrives at the detector 24 before the signal pulse 16a at detector 23, when both the time measurements are made relative to that of an initial trigger pulse. Since the digitisers 12 and 14 can each be delayed with respect to one another, each of the detected pulse components 16a and 16b are recorded such that the control and acquisition system 10, which is incorporated in detection system will ratio them to generate $I_a/I_o$. In accordance with the invention, detection and scan Method 1, described with reference to FIG. 10, is used.

Figure 18:
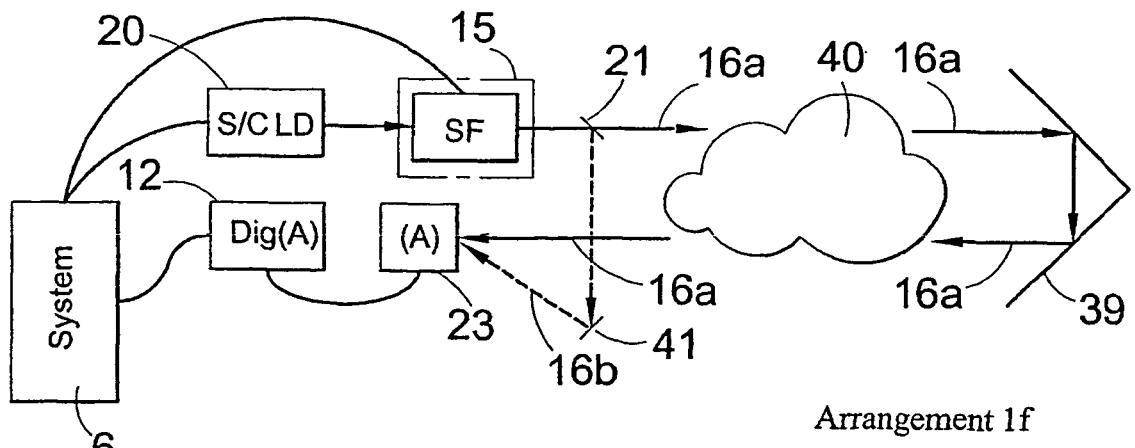
FIG. 18 is a block diagram of a modified version of the spectrometer of FIG. 17.

FIG. 18 shows a modified version of the spectrometer of FIG. 17, in which only a single detector is used. This is similar to the closed path arrangements shown in FIG. 16. In order to separate the arrival of the signal pulse 16a and the background pulse 16b at the detector 23, the transit time difference between the pulses must be greater than that of the wavelength up-chirp time or current/voltage drive pulse duration. As in embodiment 1d, since the digitiser 12 records both detected pulses 16a and 16b on the same channel, they are then separated within the digitiser 12 and processed such that the control and acquisition system 10 can ratio them generating $I_a/I_o$.

So far, the spectrometers in which the invention is embodied have been described with reference to a single mode QC laser, such as a distributed feedback (DFB) QC laser. This could, however be replaced with a multi-longitudinal mode laser. Doing this brings both advantages and disadvantages.

Figure 19A:
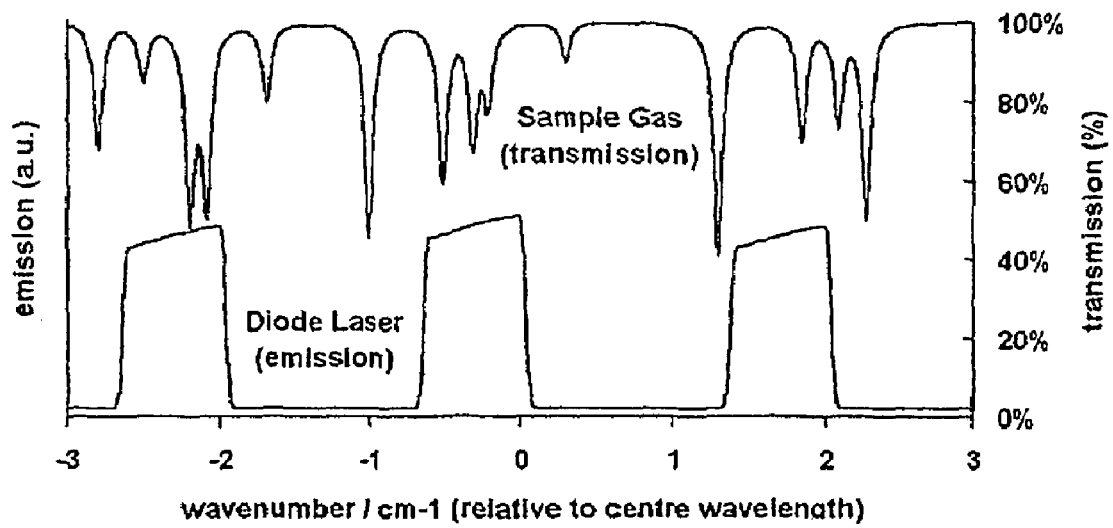
FIG. 19a shows simulated plots of part of a transmission spectrum of a complex molecule over part of the spectral range of a multi-longitudinal mode semi-conductor laser, together with the laser profile.
Figure 19B:
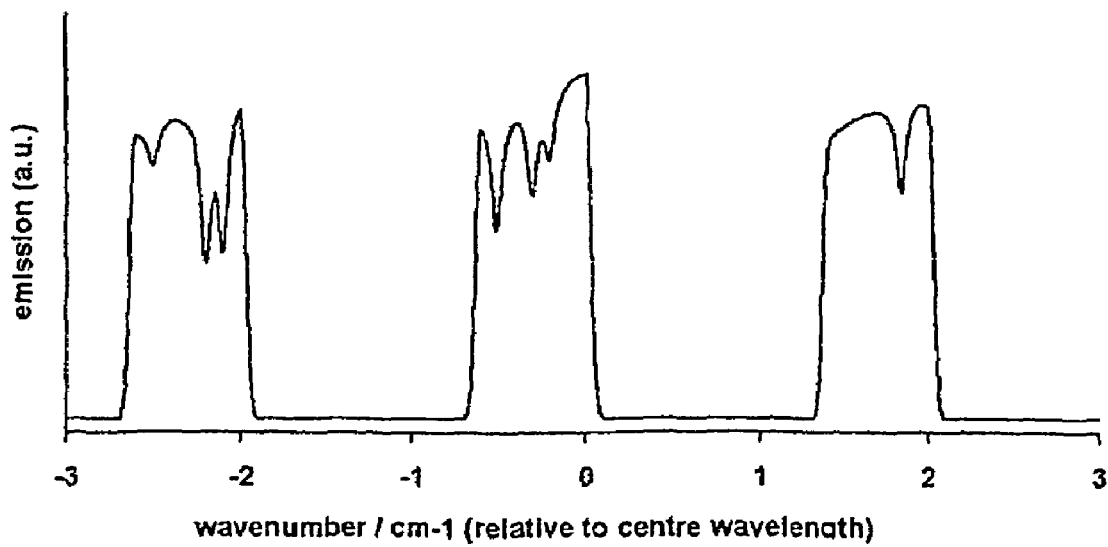
FIG. 19b shows the spectrometer output after absorption.

The principal advantage is that it widens the effective tuning range of the spectrometer. Since the absorption spectra of many of the gases of interest in sensing applications consist of groups of absorption features separated by regular intervals, the coincidences between emission and absorption lines occur at regular but frequently widely separated intervals (see Infrared Vibration-Rotation Spectroscopy, Geoffrey Duxbury, Wiley 2000 Chapters 5 and 9, for a more detailed discussion of such coincidences). This can be seen in FIGS. 19a and 19b. In FIG. 19a, the upper trace is an absorption spectrum for a sample gas. As will be appreciated, this spectrum is relatively complex. The lower trace of FIG. 19a shows the emission response of the chirped multimode QC laser, which is used to sense the sample gas. FIG. 19b shows the detected signal, from which it can be seen that there are several coincidences between the sensing laser input and the sample characteristics.

Figure 20:
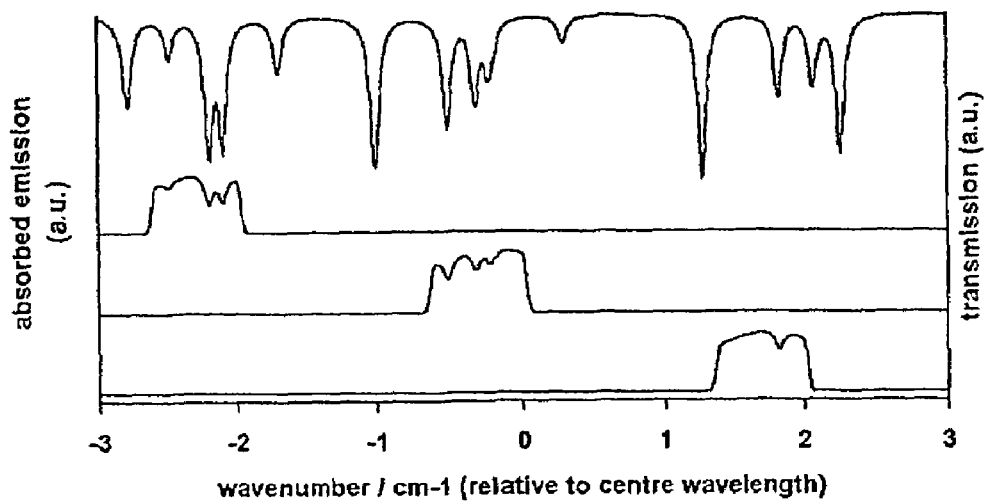
FIG. 20 shows simulated plots of part of the transmission spectrum of a complex molecule with a spectral filter used.

In the absence of a spectral filter 15 in the spectrometer of any one of FIGS. 9, 16, 17 and 18, all the spectra of FIG. 19b would be superimposed. However, the use of such a filter allows both the separation of the spectra and also the identification of the wavenumber/cm$^{-1}$ region in which they occur, as shown schematically in FIG. 20. Nevertheless, if the tuning of each mode provided by the wavenumber down-chirp were to be greater than the longitudinal mode spacing then partial overlapping of the spectra would still occur. In addition, if the spectrum of the multi-longitudinal mode laser were to be contaminated by the occurrence of off axis modes of the laser the spectral filtering method described would become difficult to implement. This is owing to the close wavenumber/cm$^{-1}$ spacing between off axis (transverse) modes, which makes it extremely difficult to design a suitable efficient broadband spectral filter.

Figure 21:
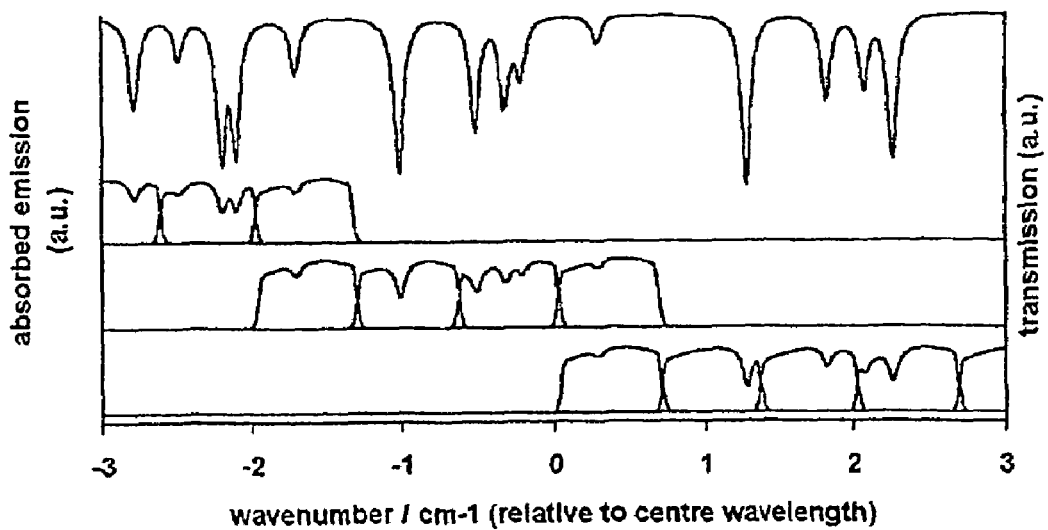
FIG. 21 shows simulated plots of part of the transmission spectrum of a complex molecule with a spectral filter used and with temperature tuning

As well as widening the effective tuning range of the spectrometer, another advantage of using a multimode laser is the possibility of using a combination of mode section and temperature tuning of individual modes to achieve complete tuning within the usable intensity low and high wavenumber modes (gain envelope) of the laser. This is shown schematically in FIG. 21.

The spectrometer in which the invention is embodied exploits the almost linear wavelength up-chirp of the intrinsic emission linewidth that occurs on a sub-microsecond time scale and therefore is able to operate a scan repetition frequency (PRF) of as high as 1 MHz. This potential gain of speed, which is an improvement of several orders of magnitude compared to prior art, would allow the present system in which the invention is embodied to fully exploit the multiplex capabilities advantages by, for example, achieving real time measurements to study processes such as fast chemical reactions (i.e. such as Free Radicals or real time atmospheric fluctuations).

The resolution of the time-resolved spectrometer in which the invention is embodied is not determined by the effective linewidth of the laser induced by the current pulse, but by the chirp rate of the laser, that is the uncertainty relation, and the temporal resolution of the detection system. In terms of the temporal response of the detection system, this is because the number of pixels (a pixel corresponds to a given time interval) into which the spectrum can be recorded within the wavelength chirp is limited by this response. The rate of this chirp is governed by the parameter. The two parameters affecting wavenumber resolution are the rate of tuning β of the intrinsic linewidth of the laser 20, and the temporal response of the detection system. Since the rate of wavenumber chirp is relatively insensitive to the pulse amplitude for this laser (see FIG. 3), the only method for achieving increased spectral resolution with the laser used here is to increase the detection bandwidth (up to the limit of the uncertainty principle). Thus the provision of a wide bandwidth detection system (500 MHz) can lead to very high spectral resolution as seen in FIG. 13.

Various modifications may be made to the arrangements described without departing from the spirit and scope of the invention. For example, it should be understood that the spectrometer arrangement in which the invention is embodied is fully capable of using an even faster detection system than that detailed or/and a semiconductor diode laser exhibiting a slower chirp rate, hence increasing further the available resolution. In a further variation, the substrate temperature of the laser could be changed. This could be done by varying the repetition rate of the applied sub-microsecond rectangular current pulse. In an alternative variation the substrate temperature can be varied by varying the base DC level of the sub-microsecond duration rectangular current drive pulses applied to the electrical contacts of the semiconductor diode laser. In addition, in the embodiments detailed, the optical beam splitting means have been described as being an optical beam splitter, however, they may instead be a dichroic mirror or other similar arrangement. It should be further understood that several semiconductor diode lasers could be implemented in the spectrometer arrangement in which the invention is embodied to achieve simultaneous measurements of different species. Further, the samples to be measured are hereinbefore described as gases, but may alternatively be aerosols.

The invention claimed is:

1. A method for sensing gases using a diode laser spectrometer, the method comprising: introducing a sample gas into a non-resonant optical cell having reflecting elements; applying a step function electrical pulse to a semiconductor diode laser to cause
the laser to output a continuous wavelength chirp for injecting into the optical cell; injecting the wavelength chirp into the optical cell; using the wavelength variation provided by the wavelength chirp as a wavelength scan, and detecting light emitted from the cell, wherein the method further includes using a chirp rate such that there is a time delay between spots on the reflecting elements sufficient to prevent light interference occurring in the optical cell.

2. A method as claimed in claim 1, wherein the duration of the pulse applied to the semiconductor diode laser is equal to or less than one microsecond.

3. A method as claimed in claim 1, wherein the duration of the pulse is less than the duration necessary for the optical output power to become zero after the drive pulse has been applied.

4. A method as claimed in claim 1 further involving varying the rate of change of wavelength per unit time.

5. A method as claimed in claim 4 wherein varying the rate of change of the wavelength per unit time involves varying the amplitude of the current/voltage drive pulse.

6. A method as claimed in claim 1 comprising adjusting the wavelength scan length.

7. A method as claimed in claim 6 wherein adjusting the wavelength scans involves varying the duration of the current/voltage drive pulse.

8. A method as claimed in claim 1 comprising temperature varying the semiconductor diode laser temperature.

9. A method as claimed in claim 1, wherein the semiconductor diode laser has output radiation having wavelengths in the region of 1 μm to 14 μm.

10. A method as claimed in claim 1 wherein the semiconductor laser is a quantum cascade laser.

11. A method as claimed in claim 1, wherein the cell is a Herriot cell.

12. A method as claimed in claim 1, wherein the amount of radiation absorbed is determined using an amplitude measurement of radiation transmitted through the sample and an amplitude measurement of a reference pulse.

13. A semiconductor diode laser spectrometer for measuring absorption by a sample, the spectrometer comprising a semiconductor diode laser; a non-resonant optical cell for containing a sample gas and having reflecting elements at either end thereof; an electric pulse generator adapted to apply a substantially step function electrical pulse to the laser to cause the laser to introduce a continuous wavelength chirp into the sample cell, and a detector for detecting light output from the cell and adapted to use the wavelength variation of the wavelength chirp as a wavelength scan, wherein the chirp rate used is such that there is a time delay between spots on the reflecting elements sufficient to prevent light interference occurring in the optical cell.

14. A spectrometer as claimed in claim 13, wherein the duration of the electrical pulse is equal to or less than 1 microsecond.

15. A spectrometer as claimed in claim 13, further comprising means for varying the rate of change of wavelength per unit time of the chirp.

16. A spectrometer as claimed in claim 15 wherein the means for varying the rate of change of the wavelength are operable to vary the amplitude of the current/voltage drive pulse.

17. A spectrometer as claimed in claim 13 further comprising means for adjusting the wavelength scan length.

18. A spectrometer as claimed in claim 17 wherein the means for adjusting the wavelength scan are operable to vary the duration of the electrical pulse.

19. A spectrometer as claimed in claim 13 further comprising means for varying a starting wavelength point of the wavelength scan.

20. A spectrometer as claimed in claim 19, wherein the means for varying a starting wavelength point are operable to vary the semiconductor diode laser base temperature.

21. A spectrometer as claimed in claim 20, wherein the means for varying the temperature of the semiconductor diode laser comprise a thermoelectric heater/cooler or means for adjusting the duty cycle or the pulse repetition frequency of the repeated current/voltage drive pulses applied to the electrical contacts of the laser diode or means for adjusting the pulse amplitude of the current/voltage drive pulses or means for adjusting the base DC level of the current/voltage drive pulses applied to the electrical contacts of the laser diode.

22. A spectrometer as claimed in claim 13, wherein a beam splitter is provided to split radiation output from the laser into two components, the first component for passing through the sample and the a second component that does not pass through the sample.

23. A spectrometer as claimed in claim 13, wherein the semiconductor diode laser emits radiation having wavelengths in the region of 1 μm to 14 μM.

24. A spectrometer as claimed in claim 13, wherein the optical cell is a Herriot cell.

25. A spectrometer as claimed in claim 13, wherein the chirp has a frequency variation of about 60 GHz.

26. A spectrometer as claimed in claim 13, wherein the applied pulse has a duration that is greater than 150 ns, in particular greater than 200 ns.

27. A spectrometer as claimed in claim 13, wherein the applied pulse has a duration that is in the range of 150 to 300 ns, preferably 200 to 300 ns.

* * * * *

UNITED STATES PATENT AND TRADEMARK OFFICE
CERTIFICATE OF CORRECTION

PATENT NO. : 7,283,243 B2
APPLICATION NO. : 10/511041
DATED : October 16, 2007
INVENTOR(S) : Nigel Langford, Geoffrey Duxbury and Erwan Normand It is certified that error appears in the above-identified patent and that said Letters Patent is hereby corrected as shown below:

Column 2, line 35, delete "runed" and insert in place thereof -- tuned --.

Column 5, line 3, delete "tuning" and insert in place thereof -- tuning. --.

Column 5, line 61, delete "1b" and insert in place thereof -- 1h --.

Column 6, line 48, delete "0.0015 cm" and insert in place thereof -- 0.0015 $cm^{-1}$ --.

Column 7, line 64, delete "use is" and insert in place thereof -- use in --.

Signed and Sealed this

Fifteenth Day of April, 2008

JON W. DUDAS
*Director of the United States Patent and Trademark Office*